(12) United States Patent　(10) Patent No.:　US 6,298,725 B1
Forrester　(45) Date of Patent:　Oct. 9, 2001

(54) METHOD FOR THE SEPARATION OF EPICYCLIC PLANET GEAR VIBRATION SIGNATURES

(75) Inventor: B. David Forrester, South Oakleigh (AU)

(73) Assignee: Aeronautical and Maritime Research Laboratory, Defence Science and Technology Organisation, Melbourne (AU)

(*) Notice: Subject to any disclaimer, the term of this patent is extended or adjusted under 35 U.S.C. 154(b) by 0 days.

(21) Appl. No.: 09/406,484

(22) Filed: Sep. 27, 1999

Related U.S. Application Data (60) Provisional application No. 60/102,754, filed on Oct. 2, 1998.

(51) Int. Cl.[7] ........................... G01M 13/02; G01H 17/00
(52) U.S. Cl. ............................................................. 73/593
(58) Field of Search ............................ 73/593, 658, 660, 73/659, 661

(56) References Cited

U.S. PATENT DOCUMENTS

| 4,931,949 | * | 6/1990 | Hernandez et al. | 73/660 |
| 5,698,788 | * | 12/1997 | Mol et al. | 73/659 |

FOREIGN PATENT DOCUMENTS

| 40638/95-B | * | 9/1996 | (AU) | 73/593 |
| 56168518-A | * | 12/1981 | (JP) | 73/593 |
| 56168519-A | * | 12/1981 | (JP) | 73/593 |
| 56168520-A | * | 12/1981 | (JP) | 73/593 |
| 56168521-A | * | 12/1981 | (JP) | 73/593 |
| 56168522-A | * | 12/1981 | (JP) | 73/593 |

* cited by examiner

*Primary Examiner*—Helen Kwok
*Assistant Examiner*—Rose M. Miller
(74) *Attorney, Agent, or Firm*—William W. Haefliger (57) ABSTRACT

The method of detecting a fault in an epicyclic gear train having ring, planet and sun gears, and a planet carrier, the steps including locating a vibration monitoring detector in association with the ring gear; operating the gear train to produce vibration detected by the detector to obtain an overall vibration signal; and timewise dividing the overall vibration signal into contributions from each planet gear.

19 Claims, 6 Drawing Sheets

(a) NEW SEPARATION TECHNIQUE
(KURTOSIS = 7.2)

Fig.2b.

(b) SNAPSHOT TECHNIQUE
(KURTOSIS = 2.4)

FIG. 3a.

(a) SNAPSHOT SEPARATION TECHNIQUE

FIG. 3b. (b) NEW PLANET SEPARATION TECHNIQUE

METHOD FOR THE SEPARATION OF EPICYCLIC PLANET GEAR VIBRATION SIGNATURES

This application claims priority from provisional application Ser. No. 60/102,754, filed Oct. 2, 1998.

BACKGROUND OF THE INVENTION

This invention relates generally to processing of vibration data obtained from epicyclic gear trains, and more particularly to a method of performing selection time filtered signal averaging on vibration data from such gear trains.

The multiplicity of identical planet gears in an epicyclic gearbox, combined with the fact that the planet gear axes move in relation to the gearbox casing, make traditional vibration analysis techniques ineffective in the diagnosis of planet gear faults. The inability to effectively diagnose faults in epicyclic gearboxes is of particular concern in helicopters, most of which use epicyclic reduction gears as the final drive to the main rotor. Accordingly, there is need for more effective fault diagnosis techniques, and particularly as respects helicopter epicyclic gear trains, for reasons that include enhancement of safety.

SUMMARY OF THE INVENTION

A new method of separating the individual planet vibration signatures in an epicyclic gearbox has now been developed, and has significant advantages over previous methods. One advantage is a significant reduction in the time required to perform sufficient separation of the planet signatures for diagnostic purposes, which makes implementation of the new method feasible in operational aircraft.

It is a major object of the invention to provide a method of performing selective time filtered signal averaging on vibration data from epicyclic gear trains. The method provides separate signal averages for the individual planets based on an estimate of each planet's contribution to the total vibration signal. This method has far superior performance to an earlier method of extracting epicyclic planet gear vibration signatures.

Signal averaging has proved to be the most useful vibration analysis tool for detecting faults in gears. However, there has been a problem in the past in applying the technique to epicyclic gearboxes. An epicyclic gearbox has a number of planet gears which all mesh with a sun and ring gear. The problems encountered when attempting to perform a signal average for components within an epicyclic gearbox are twofold. Firstly, there are multiple tooth contacts, with each planet being simultaneously in mesh with both the sun and ring gear, and secondly, the axis of the planets move with respect to both the sun and ring gear.

An earlier method of performing selective signal averaging on epicyclic gearboxes was developed and tested at the Aeronautical and Maritime Research Laboratory Defense Science and Technology Organization, Melbourne, Victoria 3001, Australia. That method was useful in detecting faults on individual planet gears; however, it was tedious to implement, required an excessively long time to perform even a small number of averages and required a selective chopping up of the time signal which proved to introduce discontinuities in the signal average.

Another method attempted to extract a representative signal average for each planet by taking a narrow window or snap-shot of the vibration signal each time a planet came past the transducer. These small packets of vibration were then assembled into appropriate buckets in a stored signal average. Typically each packet of vibration would represent a single tooth mesh and only one of these could be collected for a particular planet for each revolution of the planet carrier. To create one complete ensemble, representing a single revolution of a planet, required N, revolutions of the planet carrier, where $N_p$ is the number of teeth on a planet gear, and p is the planet gear.

Although this windowing technique appeared to work, being capable of detecting seeded faults in a test rig, there are a number of problematic aspects to it, including the following:

a) The amount of time taken to generate a usable signal average is impractical for in-service use. For instance, the Sea King helicopter main rotor gearbox has an epicyclic gear train with 196 teeth on the ring gear, 71 teeth on each of five planets and the planet carrier rotates at approximately 3.8 Hertz. This would take 71/3.8=18.68 seconds of data for each ensemble; requiring over nine minutes to perform a signal average of thirty ensembles for a single planet gear. During this time, it would be necessary to hold the torque relatively constant to ensure correct signal averaging which is totally impractical for an operational aircraft.

b) The partitioning of the vibration data into small packets creates some discontinuities at the boundaries of each bucket on reassembly. The theoretical assumption was that as the number of averages approached infinity, any discontinuities would be eliminated. However, as it is not practical to take more than a few averages, these discontinuities remain. The most worrying aspect of this is that, if the packets are exactly one tooth wide, the discontinuities appear at the mesh frequency, making any attempt to eliminate them, or even detect them, by post processing impossible.

c) In creating the signal averages for each planet, a large portion of the vibration data is neglected.

The herein disclosed alternative method for performing signal averaging for epicyclic gearbox components overcomes the problems of the earlier method. A mathematical derivation of the method is provided which shows that the averaging can be performed with no loss of information, by proportionally dividing the vibration data amongst the individual gear meshes. Practical examples are presented which show that the method has far superior performance than the earlier method and requires no longer to perform than would be required for conventional signal averaging. The present invention is also an improvement upon Australian Patent 40638/95, incorporated herein by reference.

The basic method of the invention concerns detecting a fault in an epicyclic gear train having ring, planet and sun gears, and a planet carrier, and the steps of the method include:

a) locating a vibration monitoring detector in association with the ring gear, b) operating the gear train to produce vibration detected by the detector to obtain an overall vibration signal, c) and timewise dividing the overall vibration signal into contributions from each planet gear.

Additional steps include determining time filtered signal average values with respect to the planet gears; and determining such average values substantially in accordance with an equation or equations disclosed herein.

An additional object concerns determining a time window value b(t), substantially in accordance with a further equation or equations disclosed herein.

With respect to the basic method referred to above, it is a further object to employ a rotating member in the drive to or from the gear train, employing sampling of the detector vibration, and including synchronizing such sampling with an angular reference associated with the rotating member. Such synchronizing may be effected employing one of the following: frequency multiplication or signal resampling.

A further object is to provide means elements corresponding to the steps of the method or methods referred to.

These and other objects and advantages of the invention, as well as the details of an illustrative embodiment, will be more fully understood form the following specification and drawings, in which:

DETAILED DESCRIPTION

2. Epicyclic Gearbox Vibration

Figure 1:
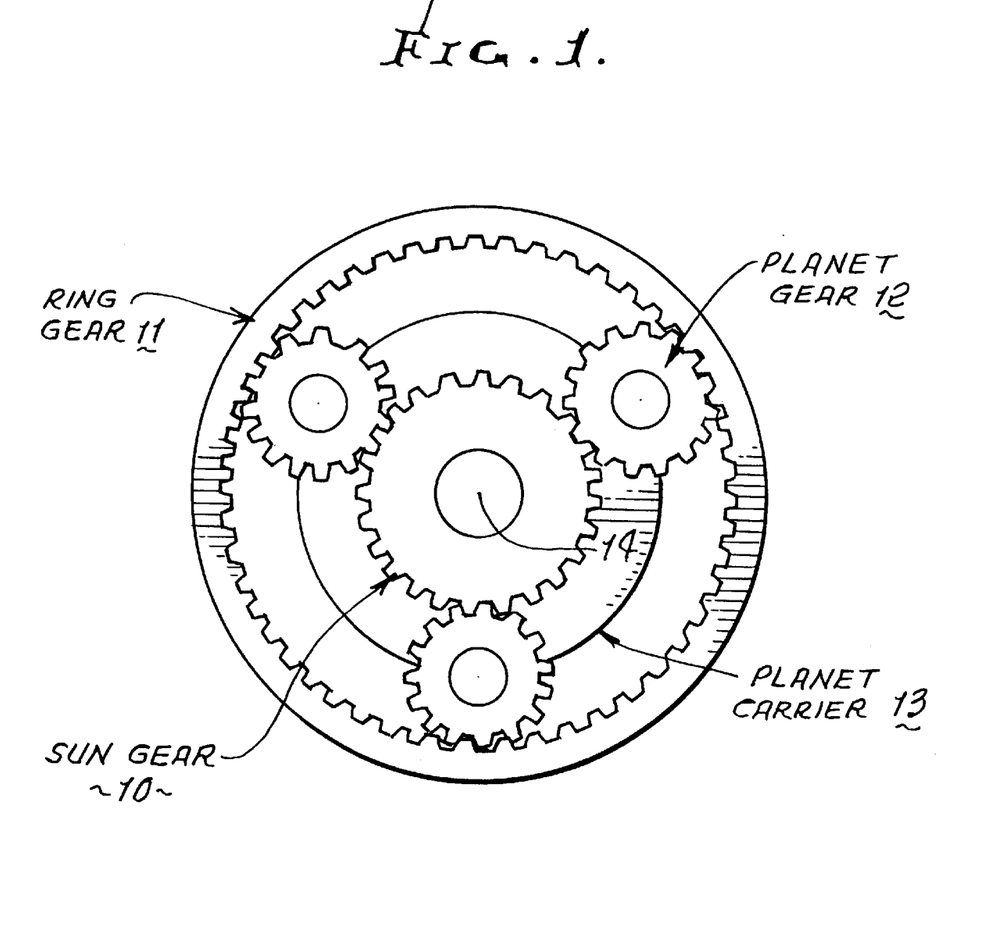
FIG. 1 is a showing of a gear train.

Epicyclic gearboxes are typically used in applications requiring a large reduction in speed (greater than three to one) at high loads, such as the final reduction in the main rotor gearbox of a helicopter. A typical epicyclic reduction gearbox has three or more planet gears each meshing with a sun and ring gear, as shown in FIG. 1. Drive is provided via the sun gear, the ring gear is stationary and the axes of the planet Sears is connected to a carrier which rotates in relation to both the sun gear and ring gear. The planet carrier provides the output of the epicyclic gear train. See the FIG. 1 gear elements 10–13, and axis 14.

2.1 Tooth Meshing Frequencies and Relative Rotations

Where $f_c$, $f_p$ and $f_s$ are the rotational frequencies of the planet carrier, planet and sun gear respectively, and there are $N_r$, $N_p$ and $N_s$ teeth on the ring, planet and sun gears respectively, the meshing frequency of the epicyclic $f_m$ is given by:

$$f_m = N_r f_c = N_p(f_p + f_c) = N_s(f_s - f_c) \quad (1)$$

The relative frequencies, $f_p + f_c$ of the planet to the carrier and $f_s - f_c$ of the sun to the carrier are:

$$f_p + f_c = f_m/N_p = f_c(N_r/N_p) \quad (2)$$

$$f_s - f_c = f_m/N_s = f_c(N_r/N_s) \quad (3)$$

2.2 Planet Pass Modulation

The only place in which it is normally feasible to locate a transducer to monitor the vibration of an epicyclic gear train is on the outside of the ring gear. This gives rise to planet pass modulation due to the relative motion of the planet gears to the transducer location.

As each planet approaches the location of the transducer, an increase in the amplitude of the vibration will be seen, reaching a peak when the planet is adjacent to the transducer then receding as the planet passes and moves away from the transducer. For an epicyclic gear train with P plants, this will occur P times per revolution of the planet carrier, resulting in an apparent amplitude modulation of the signal at frequency $Pf_c$.

2.3 Expected Epicyclic Gear Train Vibration Signal

The expected planet gear vibration signal recorded at a transducer mounted on the ring gear of an epicyclic gear train will be the sum of the individual planet gear vibrations multiplied by the planet pass modulations.

$$x(t) = \sum_{p=1}^{P} \alpha_p(t) v_p(t) \quad (4)$$

where:

$\alpha_p(t)$ is the amplitude modulation due to planet number p, and $v_p(t)$ is the tooth meshing vibration for planet p.

p identifies the individual element gear p is the number of planet gears t is time a and n are constants The amplitude modulation function $\alpha_p(t)$ (planet pass modulation) will have the same form for all planets, differing only by a time delay, and will repeat with the planet carrier rotation period $1/f_c$ $$\alpha_p(t) = a\left(t + \frac{p}{f_c P}\right) = \sum_{m=0}^{\infty} A(m) \cos\left(2\pi n f_c t + \frac{2\pi n p}{P}\right). \quad (5)$$

where $\alpha(t)$ is the planet pass modulation function and $A(m)$ is its Fourier Transform. Equation (4) can be rewritten in terms of the common planet pass modulation function giving $$x(t) = \sum_{p=1}^{P} a\left(t + \frac{p}{f_c P}\right) v_p(t). \quad (6)$$

4. New Planet Separation Technique

An Alternate method of extracting representative signal averages for each planet is to incorporate a selective (continuous) time filter into the signal averaging process. The time filter proportionally divides the overall vibration signal into the estimated contributions from each planet.

For each planet signal average $Z_p(t)$ the time window, $b(t)$, is centred at the point at which the planet is adjacent to the transducer. Signal averaging of the filtered vibration signal is performed with a period equal to the relative planet rotation $1/(f_p + f_c)$ giving, where N is the number of averages, $$\bar{z}_p(t) = \frac{1}{N} \sum_{l=0}^{N-1} b\left(t + \frac{p}{f_c P} + \frac{l}{f_p + f_c}\right) \times \left(t + \frac{l}{f_p + f_c}\right) \quad (7)$$

With careful selection of the time window characteristics and the signal averaging parameters, the separation can be performed with minimum "leakage" of vibration from other planets, no loss of vibration data and no distortion of the signal average.

4.1 Properties and Restrictions

It is shown in the "Theoretical Development", below that, where a) the separation time window is real valued and periodic with the planet carrier rotation $1/f_c$, b) the signal averaging is performed over the relative planet rotation period $1/(f_p + f_c)$ and the number of averages is an integer multiple of the number of teeth on the ring gear, $N_r$, and c) the time window b(t) is a Fourier series with less than P terms the time filtered signal average for planet P(7) reduces to, $$z_p(t) = \sum_{k=1}^{P} \overline{v}_k(t) c(p-k). \tag{8}$$

The separation function, c(n), is defined by both the applied time window b(t) and the planet pass modulation function α(t), $$c(n) = \frac{1}{2}\left(B(0)A(0) + \sum_{m=0}^{P-1} B(m)A(m)\cos\left(\frac{2\pi nn}{P}\right)\right) \tag{9}$$

where the applied time window is $$b(t) = \sum_{m=0}^{P-1} B(m)\cos(2\pi n f_c t). \tag{10}$$

Note that the summation of the time filtered signal averages $z_p(t)$ is equal to the sum of the mean planet vibration signals multiplied by a constant $$\sum_{p=1}^{P} z_p(t) = \sum_{k=1}^{P} \overline{v}_k(t) \sum_{p=1}^{P} c(p-k) = \sum_{k=1}^{P} \overline{v}_k(t)[PB(0)A(0)].$$

That is, the separation process is performed using all of the available vibration data.

One separation windows which have been found to perform well is a cosine window raised to the power of P-1. Forrester, B.D., "Method and Apparatus for Performing Selective Signal Averaging", Australian Patent 4063895

$$b(t) = (1 + \cos(2\pi f_c t))^{P-1}, \tag{11}$$

which is a tapered function, with maximum value when the planet is adjacent to the transducer and a value of 0 when the planet is furthest from the transducer.

5. Implementation

In the preceding description of the technique, it is assumed that the speed of the epicyclic gearbox is constant. In practice, even for a nominally constant speed machine, this is not always the case. To allow for speed fluctuations all analysis is done in an 'angle' domain rather than a time domain; this simply involves the substitution of an angular reference for the time based variable t.

In practice, the conversion from the time domain to the angle domain is done by synchronizing the vibration signal sampling with an angular reference on one of the shafts of the gearbox. The synchronization can be done either using phase-locked frequency multipliers or by digital resampling. Forrester, B. D., "Advanced Vibration Analysis Techniques for Fault Detection and Diagnosis in Geared Transmission Systems", PhD Thesis, Swinburne University of Technology, February 1996. McFadden, P. D., "A Model for the Extraction of Periodic Waveforms by Time Domain Averaging", Aero Propulsion Technical Memorandum 435, Department of Defense, Aeronautical Research Laboratory, March 1986.

5.2 Planet Carrier Positional Reference

For the calculation of the time windowed signal averages (equation 7) a planet carrier positional reference is required to set the starting time (t=0) to a point at which one of the planets (p=P) is adjacent to the transducer. The positional reference can be obtained either by using a shaft encoder/tacho on the planet carrier (usually the output of the gearbox) or by software synchronization to the planet pass modulation signal.

In the case where a carrier positional reference is not directly available, the planet carrier position can be estimated by examining the planet pass modulation. This involves performing a signal average of planet carrier (ring gear) vibration. As each planet passes the transducer location the vibration level increases, giving an amplitude modulation of the vibration signal. Demodulation of the ring gear signal average about the gear mesh vibration (McFadden, P. D., "Examination of a Technique for the Early Detection of Failure in Gears by Signal Processing of the Time Domain Average of the Meshing Vibration". Mechanical Systems and Signal Processing, Vol.1(2).pp. 173–183, 1987) is used to determine the modulation peaks as each planet gear passes the transducer location. The point with the maximum amplitude in the demodulated signal average is selected as the zero point for the planet carrier positional reference.

6. Example

The following example is from a recorded vibration signal of an epicyclic gearbox with three planet gears each having 32 teeth, a sun gear with 28 teeth and a ring gear having 95 teeth. A small fault was implanted on one tooth on one of the planet gears. McFadden, P. D. and Howard, L. M., "The Detection of Seeded Faults in an Epicyclic Gearbox by Signal Averaging of the Vibration", Propulsion Report 183, Department of Defense, Aeronautical Research Laboratory, October 1990. McFadden and Howard were able to detect this fault using the snapshot technique over 32 ensembles. This represents approximately 240 seconds (4 minutes) of run time.

Figure 2A:
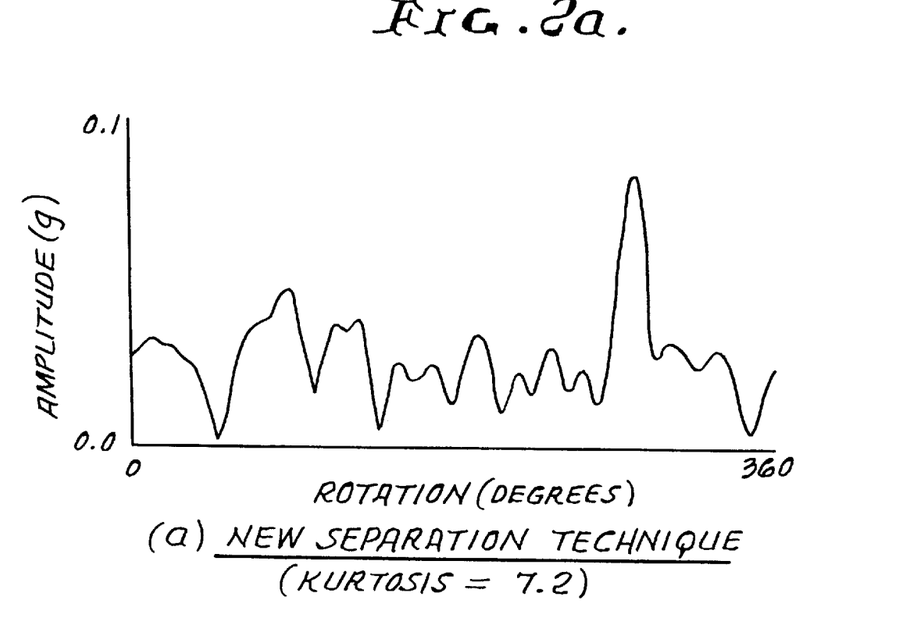
FIGS. 2a and 2b shows two diagrams, depicting signal amplitude as a function of rotation.
Figure 2B:
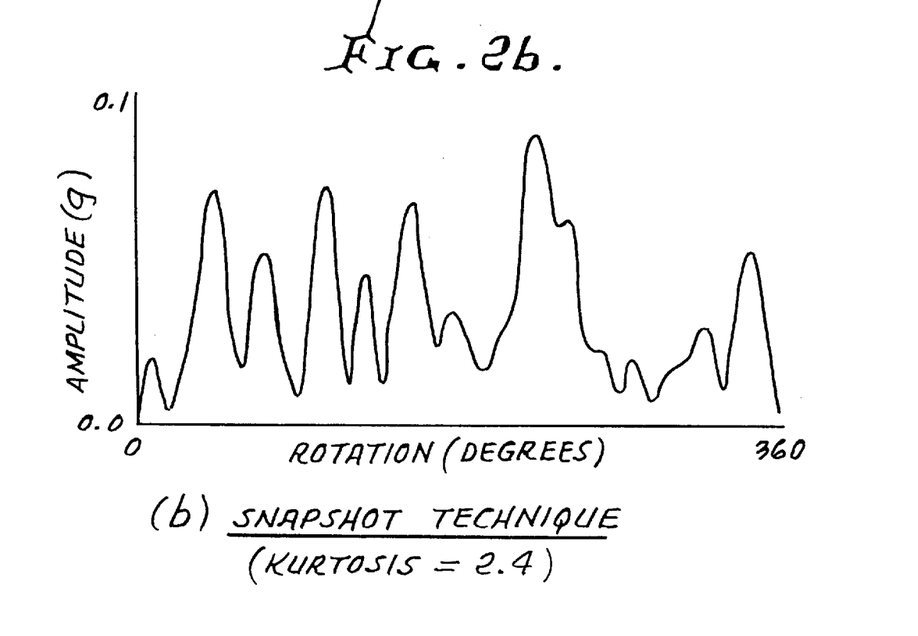

FIG. 2 shows the results obtained by performing a narrow band envelope enhancement. McFadden, P. D., "Examination of a Technique for the Early Detection of Failure in Gears by Signal Processing of the Time Domain Average of the Meshing Vibration", on the separated signal averages for the faulty planet using (a) the new separation technique with the time window defined in equation (11), and (b) the snapshot technique. For this example, the analysis time is only 75 seconds (10×32 revolutions of the planet carrier). This is less than one third of the time used in the above referenced (McFadden P. D., and Howard, L. M., "The Detection of Seeded Faults in an Epicyclic Gearbox by Signal Averaging of the Vibration", Propulsion Report 183, Department of Defense, Aeronautical Research Laboratory, October 1990). The 'kurtosis' of the narrow band envelopes is used as a measure of local variation in the tooth meshing behavior. A kurtosis value greater than 4.5 is considered to be a clear indication of a local defect and a value below 3.5 indicates a 'good' gear.

The new technique gives a kurtosis of 7.2, clearly indicating the presence of the fault. Over the same analysis period the snapshot technique (kurtosis=2.4) gives no indication of the fault.

Figure 3A:
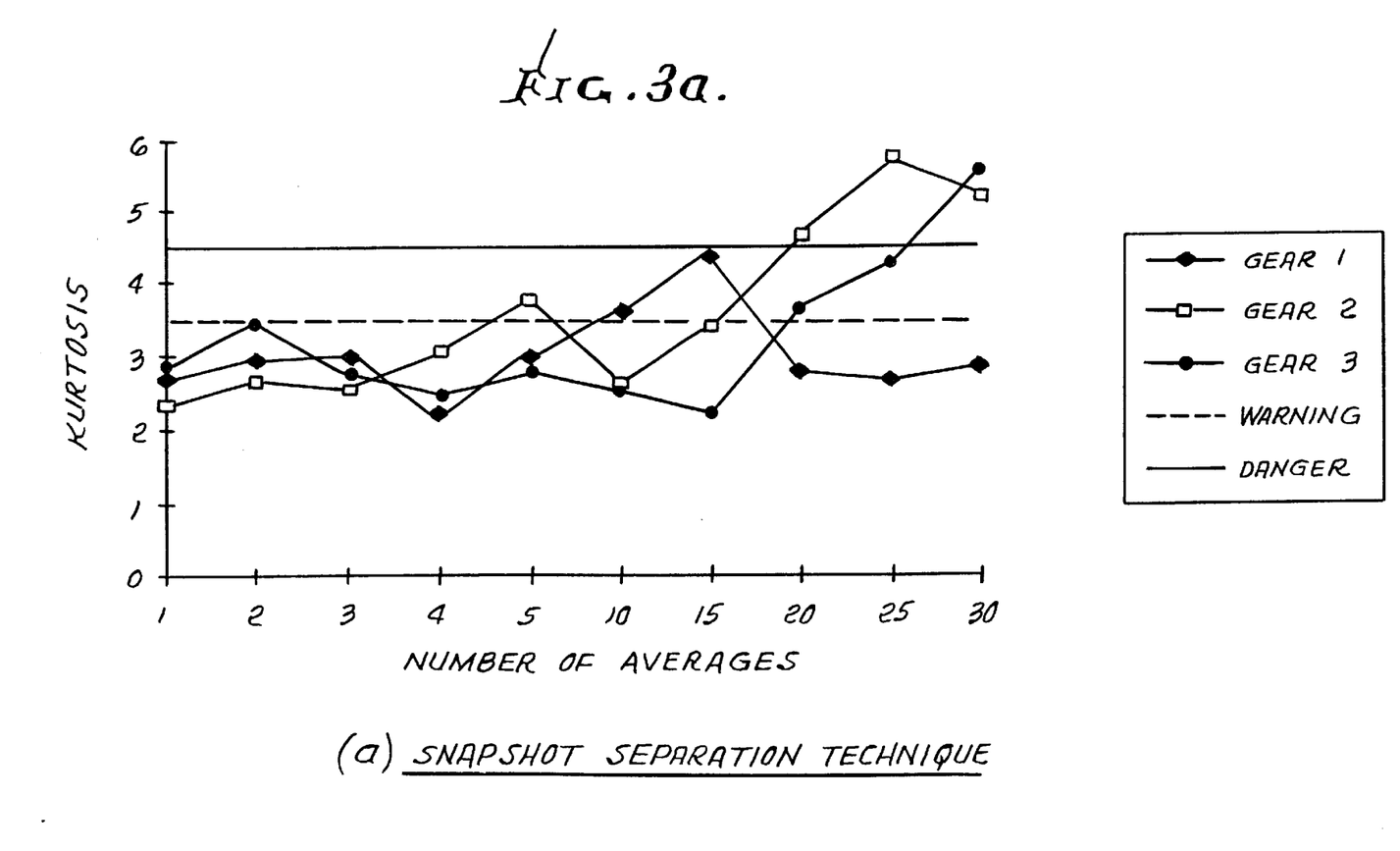
FIGS. 3a and 3b shows two diagrams depicting gear kurtosis values as a function of number of averages.
Figure 3B:
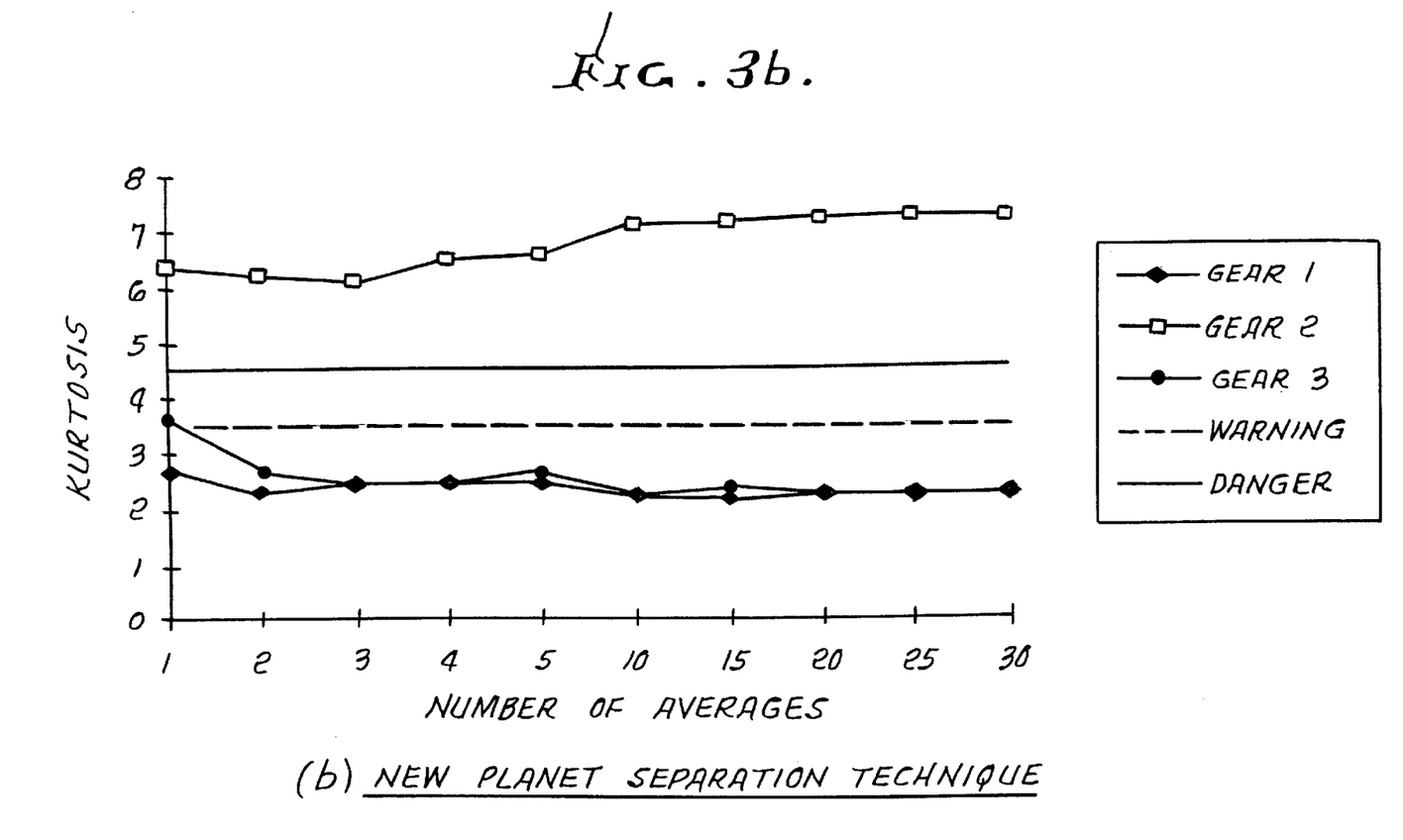

FIG. 3 shows the comparative performance of (a) the McFadden & Howard 'snapshot' technique and (b) the new planet separation technique over varying lengths of data for the planet gear fault test described above. The graphs shows the 'kurtosis' of all three planet gears versus the number of 'averages' used for the analysis; the graphs also include the warning (kurtosis=3.5) and danger (kurtosis–4.5) levels for reference. Each 'average' represents 32 revolutions of the planet carrier (95 periods of the relative planet gear rotation) which, in this case, is approximate 7.5 seconds of data. Identical data and planet carrier positions reference has been used for both methods.

As can be seen, the difference in performance of the two methods is striking. The 'snapshot' technique. FIG. 3(a), behaves in an erratic fashion; only giving a clear indication of a fault on gear 2 after 20 'averages' and with poor separation of the planets (i.e., a false fault indication is seen on gear 3). In direct contrast to this erratic behavior, the new planet separation technique, as seen in FIG. 3(b), shows a remarkably efficient and stability. After only 1 'average', a very clear fault indication is given on gear 2 with relatively good separation (gear 3 just above warning level). After only 3 'averages' excellent fault detection and planet separation has been achieved (no evidence of fault in the undamaged gears). After 10 'averages', the new planet separation technique has completely stabilized and very little change occurs with further averaging.

7. FURTHER DESCRIPTION

Figure 4:
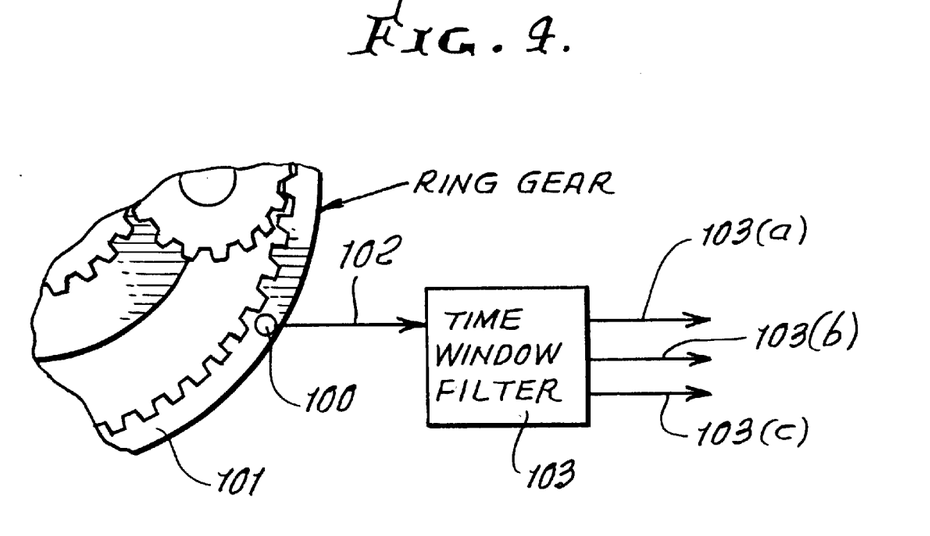
FIG. 4 is a block diagram.

FIG. 4 shows the provision of a transducer 100 positioned on the ring gear 101, such as at the outside of a ring gear. The overall vibration output signal at 102 is processed at 103, as by proportionally dividing the signal 102 into estimated contributions from each planet. See Equation (7) above. The three planet signal average signals are indicated at 103(a), 103(b) and 103(c) in FIG. 4. See also Equations (8), (9) and (10) defining signal processing, further.

Figure 5:
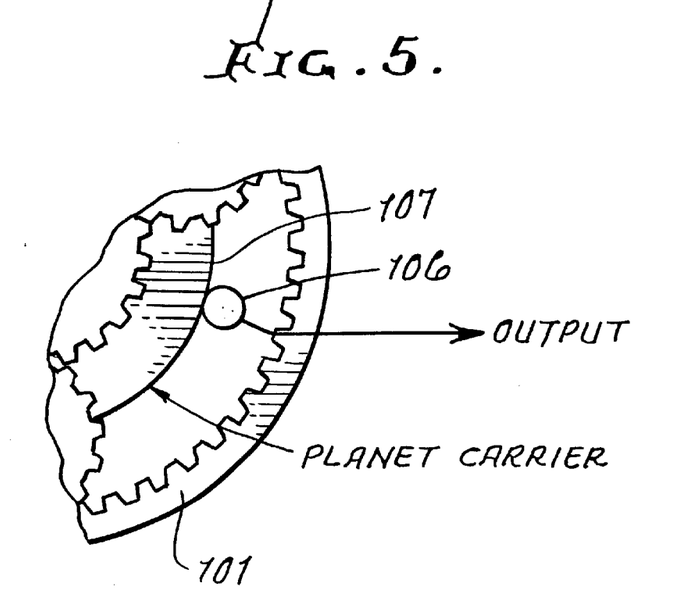
FIG. 5 is a diagram showing location of an encoder.

FIG. 5 shows use of a shaft encoder/tachometer 106 on the planet 107 carrier 107, as at the output of the gearbox.

Figure 6:
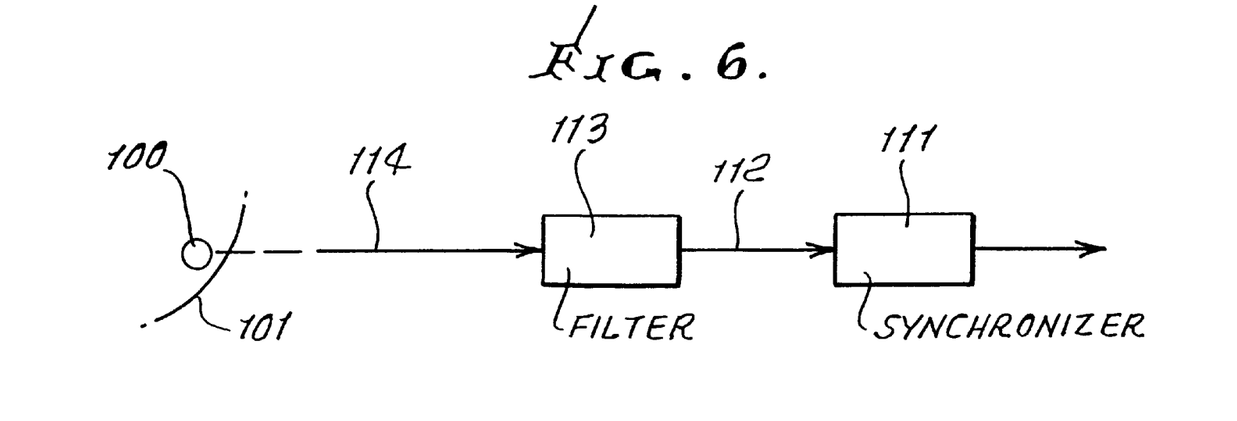
FIGS. 6 and 7 are block diagrams.

FIG. 6 shows use of synchronizer software 111 to provide synchronization to the planet pass modulation signal 112. The latter is supplied from planet pass filter 113 ad described above receiving input from the signal 114 output from the transducer 100 at the ring gear.

Figure 7:
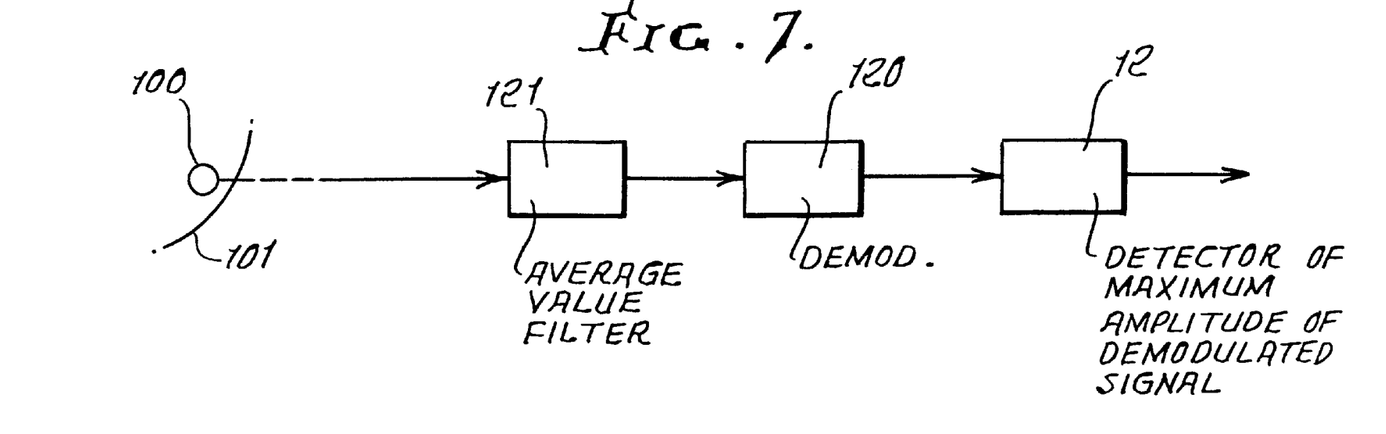

FIG. 7 shows use of a demodulator 120 receiving input from the average value filter indicated at 121, of the ring gear signal from transducer 100. See paragraph 5 above.

8. Theoretical Development

Assuming that all vibration which is not synchronous with the relative planet rotation will tend toward zero with the signal averaging process [4,5], the same filtered signal average (7) using the time window b(t) taken over N periods of the relative planet rotation, $1/(f_p+f_c)$, can be expressed as $$\bar{z}_p(t) = \frac{1}{N}\sum_{l=0}^{N-1} b\left(t + \frac{p}{f_c P} + \frac{l}{f_p + f_c}\right) \times \left(t + \frac{l}{f_p + f_c}\right) \quad \text{(A.1)}$$

$$= \frac{1}{N}\sum_{l=0}^{N-1} b\left(t + \frac{p}{f_c P} + \frac{lN_p}{f_c + f_r}\right)\sum_{k=1}^{P} a\left(t + \frac{k}{f_c P} + \frac{lN_p}{f_c N_r}\right) v_k\left(t + \frac{l}{f_p + f_c}\right)$$

$$= \sum_{k=1}^{P} \bar{v}_k(r) \frac{1}{N}\sum_{l=0}^{N-1} b\left(t + \frac{p}{f_c P} + \frac{lN_p}{f_c N_r}\right) a\left(t + \frac{k}{f_c P} + \frac{lN_p}{f_c N_r}\right)$$

where $v_k(t)$ is the mean vibration value for planet k, which repeats with period $1(f_p+f_c)$ and $\alpha(t)$ is the planet pass modulation (5).

Condition $\alpha$): $b(t)$ is real valued and periodic in $1/f_c$ Under the condition that $b(t)$ is real valued and period in $1/f$, $$b(t) = \sum_{m=0}^{\infty} B(m)\cos(2\pi m f_c t), \quad (A.2)$$

the time filtered signal average becomes $$\bar{z}_p(t) = \sum_{k=1}^{P} \bar{v}_k(t)\Psi(p, k, t) \quad (A.3)$$

where $$\Psi(p, k, t) = \sum_{m=0}^{\infty} \sum_{n=0}^{\infty} B(m)A(n) \frac{1}{2N} \sum_{l=0}^{N-1}$$

$$\left[ \cos\left(2\pi(m+n)f_c t + \frac{2\pi(mp+nk)}{P} + \frac{2\pi l(m+n)N_p}{N_r}\right) + \cos\left(2\pi(m-n)f_c t + \frac{2\pi(mp+nk)}{P} + \frac{2\pi l(m-n)N_p}{N_r}\right) \right]$$

$$= \sum_{m=0}^{\infty} \sum_{n=0}^{\infty} B(m)A(n) \frac{1}{2N} \sum_{l=0}^{N-1}$$

$$\left[ \cos\left(2\pi(m+n)f_c t + \frac{2\pi(mp+nk)}{P}\right)\cos\left(\frac{2\pi l(m+n)N_p}{N_r}\right) - \sin\left(2\pi(m+n)f_c t + \frac{2\pi(mp+nk)}{P}\right)\sin\left(\frac{2\pi l(m+n)N_p}{N_r}\right) + \cos\left(2\pi(m-n)f_c t + \frac{2\pi(mp-nk)}{P}\right)\cos\left(\frac{2\pi l(m-n)N_p}{N_r}\right) - \sin\left(2\pi(m-n)f_c t + \frac{2\pi(mp-nk)}{P}\right)\sin\left(\frac{2\pi l(m-n)N_p}{N_r}\right) \right]$$

Condition b): number of average is an integer multiple of $N_r$.

If the number of averages N is an integer multiple of the number of teeth on the ring gear, $N_r$, then, since $$\frac{1}{iN_r} \sum_{l=0}^{iN_r-1} \cos\left(\frac{2\pi l(m+n)N_p}{N_r}\right) = \delta(m+n) \quad (A.5)$$

and $$\frac{1}{iN_r} \sum_{l=0}^{iN_r-1} \sin\left(\frac{2l(m\ n)N_p}{N_r}\right) =,$$

we have $$\Psi(p, k, t) = \frac{1}{2} \sum_{m=0}^{\infty} \sum_{n=0}^{\infty} B(m)A(n) \quad (A.6)$$

$$\left[ \cos\left(2\pi(m+n)f_c t + \frac{2\pi(mp+nk)}{P}\right)\delta(m+n) + \cos\left(2\pi(m-n)f_c t + \frac{2\pi(mp-nk)}{P}\right)\delta(m-n) \right]$$

$$= \frac{1}{2} \sum_{m=0}^{\infty} B(m)A(-m)\cos\left(\frac{2\pi n(p-k)}{P}\right) +$$

$$B(m)A(m)\cos\left(\frac{2\pi m(p-k)}{P}\right) \Big]$$

$$= \frac{1}{2}\left[ B(0)A(0) + \sum_{m=0}^{\infty} B(m)A(m)\cos\left(\frac{2\pi m(p-k)}{P}\right) \right].$$

Condition c): $b(t)$ is a Fourier series with less than P terms

The summation in m is a discrete Fourier series with period P and, to avoid aliasing, the number of terms in the series needs to be limited to less than P. This is done by setting the limitation that the time window function $b(t)$ be a Fourier series of less than P terms, $$b(t) = \sum_{m=0}^{P-1} B(m)\cos(2\pi m f_c t) \quad (A.7)$$

and the time filtered signal average $\bar{z}_p(t)$ over $iN_r$ averages with period $1/(f_p+f_c)$ becomes $$\bar{z}_p(t) = \sum_{k=1}^{P} \bar{v}_k(t) c(p-k) \quad (A.8)$$

where $$c(n) = \frac{1}{2}\left( B(0)A(0) + \sum_{m=0}^{P-1} B(m)A(m)\cos\left(\frac{2\pi mn}{P}\right) \right). \quad (A.9)$$

I claim:

1. In the method of detecting a fault in an epicyclic gear train having ring, planet and sun gears, and a planet carrier, the steps that include:
    a) locating a vibration monitoring detector in association with the ring gear,
    b) operating the gear train to produce vibration detected by the detector to obtain an overall vibration signal,
    c) and timewise dividing the overall vibration signal into contributions from each planet gear.

2. The method of claim 1 including determining time filtered signal average values with respect to said planet gears.

3. The method of claim 2 wherein said time filtered signal average values are determined substantially in accordance with the following equation (7) in the above, represented as follows:

$$\bar{z}_p(t) = \frac{1}{N}\sum_{l=0}^{N-1} b\left(t + \frac{p}{f_c P} + \frac{l}{f_p + f_c}\right) \times \left(t + \frac{l}{f_p + f_c}\right)$$

where:
   v=number of rotations of planet gears over which signal averaging is performed
   b=time window b(t), a Fourier series with less than P terms (see Equation 10 above)
   x=planet gear vibration signal
   p=the planet gear
   $f_c$=frequency of rotation of gears that planets carry
   P=the planet gear
   $f_p$=frequency of rotation of planet gear
   l=integer representing the ensemble number
   t=time.

4. The method of claim 2 wherein the time filtered signal average value for planet p is determined substantially in accordance with the following equation (8) in the above, represented as follows:

$$\bar{z}_p(t) = \sum_{k=1}^{P} \bar{v}_k(t) c(p - k)$$

where:
   p=the planet
   $v_k(t)$=vibration signal from the $k^{th}$ planet
   c=separation function
   k=planet number
   p=number of planet gears
   t=time.

5. The method of claim 4 wherein said determination is effected employing a separation function c(n) substantially in accordance with equation (9) in the above, represented as follows:

$$c(n) = \frac{1}{2}\left(B(0)A(0) + \sum_{m=0}^{P-1} B(m)A(m)\cos\left(\frac{2\pi mn}{P}\right)\right)$$

where:
   B(o)=applied time window function constant value for planet O
   A(o)=planet pass modulation function constant value for planet O
   P=number of planet gears
   m=integer representing planet number
   B(m)=applied time window function constant value for planet O
   A(m)=planet pass modulation function constant value for planet m
   n=ensemble number.

6. The method of claim 5 wherein a time window value b(t), is applied, substantially in accordance with equation (10) in the above, represented as follows:

$$b(t) = \sum_{m=0}^{P-1} B(m)\cos(2\pi m f_c t).$$

7. The method of claim 5 wherein a time window value b(t), is applied, substantially in accordance with equation (11) in the above, represented as follows:

$$b(t) = (1 + \cos(2\pi f_c t))^{P-1}$$

where:
   l=integer representing the ensemble number
   P=number of planet gears
   $f_c$=frequencies of rotation of gear that planet carries
   t=time.

8. The method of claim 7 wherein a narrow band envelope kurtosis value is employed as a measure of local variation in gear tooth meshing behaviour, wherein a kurtosis value greater than 4.5 indicates a local defect exists, and wherein a kurtosis value below 3.5 indicates an acceptable gear.

9. The method of claim 1 wherein a rotating member is employed in the drive to or from the gear train, and said operating step is effected employing sampling of the detector vibration, and including synchronizing said sampling with an angular reference associated with said rotating member.

10. The method of claim 9 wherein said synchronizing is effected employing one of the following:
    i) frequency multiplication
    ii) signal resampling.

11. In apparatus for detecting a fault in an epicyclic gear train having ring, planet and sun gears, and a planet carrier, the combination that comprises:
    a) a vibration monitoring detector in association with the ring gear,
    b) the gear train operated and the detector operated to produce vibration detected by the detector to obtain an overall vibration signal,
    c) and means for timewise dividing the overall vibration signal into contributions from each planet gear.

12. The combination of claim 11 including means for determining signal average values with respect to said planet gears.

13. The combination of claim 12 wherein said means includes filter means to determine said average values substantially in accordance with equation (7) above, represented as follows:

$$\bar{z}_p(t) = \frac{1}{N}\sum_{l=0}^{N-1} b\left(t + \frac{p}{f_c P} + \frac{l}{f_p + f_c}\right) \times \left(t + \frac{l}{f_p + f_c}\right)$$

where:
   v=number of rotations of planet gears over which signal averaging is performed b=time window b(t), a Fourier series with less than P terms (see Equation 10 above)

x=planet gear vibration signal p=the planet gear $f_c$=frequency of rotation of gears that planets carry P=number of planet gears $f_p$=frequency of rotation of planet gear l=integer representing the ensemble number t=time.

14. The combination of claim 12 wherein said means includes filter means to determine said average values substantially in accordance with equation (8) above, represented as follows:

$$\bar{z}_p(t) = \sum_{k=1}^{P} \bar{v}_k(t)c(p-k).$$

where:

p=the planet $v_k(t)$=vibration signal from the $k^{th}$ planet c=separation function k=planet number P=number of planet gears t=time.

15. The combination of claim 14 wherein said filter means includes means providing a separation function c(n) substantially in accordance with equation (9) in the above, represented as follows:

$$c(n) = \frac{1}{2}\left(B(0)A(0) + \sum_{m=0}^{P-1} B(m)A(m)\cos\left(\frac{2\pi mn}{P}\right)\right)$$

where:

B(o)=applied time window function constant value for planet O

A(o)=planet pass modulation function constant value for planet O

P=number of planet gears m=integer representing planet number

B(m)=applied time window function constant value for planet O

A(m)=planet pass modulation function constant value for planet m n=ensemble number.

16. The combination of claim 15 wherein said filter means includes providing a time window value b(t), which is applied, said value b(t) represented substantially in accordance with equation (10) in the above, as follows:

$$b(t) = \sum_{m=0}^{P-1} B(m)\cos(2\pi m f_c t).$$

17. The combination of claim 15 wherein said filter means includes means providing a time window value b(t), which is applied, said value b(t) represented substantially in accordance with equation (11) in the above, as follows:

$$b(t) = (1+\cos(2\pi f_c t))^{P-1}$$

where:

l=integer representing the ensemble number

P=number of planet gears $f_c$=frequencies of rotation of gear that planet carries t=time.

18. The combination of claim 11 wherein a rotating member is employed in the drive to or from the gear train, and said operating step is effected employing means for sampling of the detector vibration, and including means for synchronizing said sampling with an angular reference associated with said rotating member.

19. The method of claim 18 wherein said means for synchronizing includes one of the following:

iii) frequency multiplication means iv) signal resampling means.

* * * * *